(12) United States Patent
Stocklin et al.

(10) Patent No.: US 9,566,227 B2
(45) Date of Patent: Feb. 14, 2017

(54) COSMETIC COMPOSITION COMPRISING A MUCONOPEPTIDE

(71) Applicant: ACTIVEN, Lausanne (CH)

(72) Inventors: Reto Stocklin, Avusy (CH); Jean-Marc Le Doussal, Lausanne (CH); Louis Lamy, Orlienas (FR); Bethsabee Coutaz, Neuilly sur Seine (FR)

(73) Assignee: ACTIVEN, Lausanne (CH)

( * ) Notice: Subject to any disclaimer, the term of this patent is extended or adjusted under 35 U.S.C. 154(b) by 0 days.

(21) Appl. No.: 14/391,455

(22) PCT Filed: Apr. 15, 2013

(86) PCT No.: PCT/EP2013/057850
§ 371 (c)(1),
(2) Date: Oct. 9, 2014

(87) PCT Pub. No.: WO2013/153236
PCT Pub. Date: Oct. 17, 2013

(65) Prior Publication Data
US 2015/0132235 A1 May 14, 2015

Related U.S. Application Data

(60) Provisional application No. 61/623,913, filed on Apr. 13, 2012.

(30) Foreign Application Priority Data

Apr. 17, 2012 (WO) .................. PCT/EP2012/057026

(51) Int. Cl.
*A61K 8/64* (2006.01)
*A61Q 19/08* (2006.01)
*A61K 38/17* (2006.01)

(52) U.S. Cl.
CPC ............. *A61K 8/64* (2013.01); *A61K 38/1767* (2013.01); *A61Q 19/08* (2013.01); *A61K 2800/83* (2013.01)

(58) Field of Classification Search
None
See application file for complete search history.

(56) References Cited

U.S. PATENT DOCUMENTS

| 2003/0050234 A1 | 3/2003 | Olivera et al. |
| 2004/0204362 A1 | 10/2004 | Olivera et al. |
| 2008/0005031 A1 | 1/2008 | Kamio et al. |
| 2010/0021510 A1 | 1/2010 | Serraima et al. |

FOREIGN PATENT DOCUMENTS

| EP | 2123673 | 11/2009 |
| WO | 02/07678 | 1/2002 |
| WO | 2004/099238 | 11/2004 |
| WO | 2006/047900 | 5/2006 |
| WO | 2007/054785 | 5/2007 |
| WO | 2007/071448 | 6/2007 |
| WO | 2009/012376 | 1/2009 |
| WO | 2011/048443 | 4/2011 |

OTHER PUBLICATIONS http://www.aocd.org/?page=Hyperpigmentation, accessed Oct. 20, 2015.*
Carmago et al. "Botulism toxin for facial wrinkles" The Cochrane Library 2014, Issue 9.*
International Search Report dated Jan. 8, 2014, corresponding to PCT/EP2013/057850.
Iti, et al.; "Status of Surfactants as Penetration Enhancers in Transdermal Drug Delibvery"; vol. 4, No. 1; Feb. 9, 2012, pp. 1-11.
Gayathri Krishnan, et al.; "Enhanced Transdermal Delivery of 5-Aminolevulinic Acid and a Dipeptide by Iontophoresis"; vol. 96, No. 2, 2011; pp. 166-171.
Philippe Favreau, et al.; "Marine Snail Venoms: Use and Trends in Receptor and Channel Neuropharmacology"; vol. 9, No. 5; Oct. 2009; pp. 594-601.
Philippe Favreau, et al.; "A Novel—Conopeptide, CnIIIC, Exerts Potent and Preferential Inhibition NaV1.2/1.4 Channels and Blocks Neuronal Nicotinic Acetylcholine Receptors"; vol. 166, No. 5; Jul. 2012; pp. 1654-1668.

* cited by examiner

Primary Examiner — James H Alstrum Acevedo
Assistant Examiner — Tara Martinez
(74) Attorney, Agent, or Firm — Young & Thompson

(57) ABSTRACT

A cosmetic composition including as an active substance a cosmetically effective amount of at least one mu-conotoxin peptide It further concerns a composition wherein the mu-conotoxin peptide is Argninine, lysine polypeptide, CAS Number: 937286-43-6, Molecular formula $C_{92}, H_{139}, N_{35}, O_{28}, S_6$ acetate salt (molar mass 2376 g/mol.). Also, the use of the composition to improve the mechanical properties of the skin, tonicity and/or firmness and/or elasticity of the skin.

3 Claims, 2 Drawing Sheets

SEQUENCE LISTING

```
<160> NUMBER OF SEQ ID NOS: 3

<210> SEQ ID NO 1
<211> LENGTH: 23
<212> TYPE: PRT
<213> ORGANISM: Conus sp.
<220> FEATURE:
<221> NAME/KEY: MISC_FEATURE
<222> LOCATION: (1)..(1)
<223> OTHER INFORMATION: X is any N-modified amino acid
<220> FEATURE:
<221> NAME/KEY: MISC_FEATURE
<222> LOCATION: (5)..(5)
```

```
<223> OTHER INFORMATION: X is any acidic amino acid or any of its amide
      form
<220> FEATURE:
<221> NAME/KEY: MISC_FEATURE
<222> LOCATION: (7)..(7)
<223> OTHER INFORMATION: Proline or 3-hydroxyl proline
<220> FEATURE:
<221> NAME/KEY: MISC_FEATURE
<222> LOCATION: (8)..(8)
<223> OTHER INFORMATION: X is any basic amino acid
<220> FEATURE:
<221> NAME/KEY: MISC_FEATURE
<222> LOCATION: (11)..(11)
<223> OTHER INFORMATION: X is any non-aromatic hydroxyl amino acid
<220> FEATURE:
<221> NAME/KEY: MISC_FEATURE
<222> LOCATION: (12)..(12)
<223> OTHER INFORMATION: X is any non-aromatic hydroxyl amino acid
<220> FEATURE:
<221> NAME/KEY: MISC_FEATURE
<222> LOCATION: (13)..(13)
<223> OTHER INFORMATION: X is any basic amino acid
<220> FEATURE:
<221> NAME/KEY: MISC_FEATURE
<222> LOCATION: (14)..(14)
<223> OTHER INFORMATION: X is any aromatic amino acid
<220> FEATURE:
<221> NAME/KEY: MISC_FEATURE
<222> LOCATION: (16)..(16)
<223> OTHER INFORMATION: X is any basic amino acid
<220> FEATURE:
<221> NAME/KEY: MISC_FEATURE
<222> LOCATION: (17)..(17)
<223> OTHER INFORMATION: X is any acidic amino acid, or any of its amide
      form
<220> FEATURE:
<221> NAME/KEY: MISC_FEATURE
<222> LOCATION: (18)..(18)
<223> OTHER INFORMATION: X is any basic amino acid, or any
      sulfur-containing amino acid
<220> FEATURE:
<221> NAME/KEY: MISC_FEATURE
<222> LOCATION: (19)..(19)
<223> OTHER INFORMATION: X is any hydrophobic or apolar amino acid, or
      any non-aromatic hydroxyl amino acid
<220> FEATURE:
<221> NAME/KEY: MISC_FEATURE
<222> LOCATION: (20)..(20)
<223> OTHER INFORMATION: X is any basic amino acid
<220> FEATURE:
<221> NAME/KEY: MISC_FEATURE
<222> LOCATION: (23)..(23)
<223> OTHER INFORMATION: X is any apolar amino acid, or an amide group

<400> SEQUENCE: 1

Xaa Gly Cys Cys Xaa Gly Pro Xaa Gly Cys Xaa Xaa Xaa Xaa Cys Xaa
1               5                   10                  15

Xaa Xaa Xaa Xaa Cys Cys Xaa
            20

<210> SEQ ID NO 2
<211> LENGTH: 23
<212> TYPE: PRT
<213> ORGANISM: Conus sp.
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 2

Xaa Gly Cys Cys Asn Gly Pro Lys Gly Cys Ser Ser Lys Trp Cys Arg
```

```
1               5                   10                  15
Asp His Ala Arg Cys Cys Xaa
                20

<210> SEQ ID NO 3
<211> LENGTH: 22
<212> TYPE: PRT
<213> ORGANISM: Conus sp.
<220> FEATURE:
<221> NAME/KEY: MISC_FEATURE
<222> LOCATION: (1)..(1)
<223> OTHER INFORMATION: X is any N-modified amino acid
<220> FEATURE:
<221> NAME/KEY: MISC_FEATURE
<222> LOCATION: (5)..(5)
<223> OTHER INFORMATION: X is any acidic amino acid or any of its amide
      form
<220> FEATURE:
<221> NAME/KEY: MISC_FEATURE
<222> LOCATION: (7)..(7)
<223> OTHER INFORMATION: Proline or 3-hydroxyl proline
<220> FEATURE:
<221> NAME/KEY: MISC_FEATURE
<222> LOCATION: (8)..(8)
<223> OTHER INFORMATION: X is any basic amino acid
<220> FEATURE:
<221> NAME/KEY: MISC_FEATURE
<222> LOCATION: (11)..(11)
<223> OTHER INFORMATION: X is any non-aromatic hydroxyl amino acid
<220> FEATURE:
<221> NAME/KEY: MISC_FEATURE
<222> LOCATION: (12)..(12)
<223> OTHER INFORMATION: X is any non-aromatic hydroxyl amino acid
<220> FEATURE:
<221> NAME/KEY: MISC_FEATURE
<222> LOCATION: (13)..(13)
<223> OTHER INFORMATION: X is any basic amino acid
<220> FEATURE:
<221> NAME/KEY: MISC_FEATURE
<222> LOCATION: (14)..(14)
<223> OTHER INFORMATION: X is any aromatic amino acid
<220> FEATURE:
<221> NAME/KEY: MISC_FEATURE
<222> LOCATION: (16)..(16)
<223> OTHER INFORMATION: X is any basic amino acid
<220> FEATURE:
<221> NAME/KEY: MISC_FEATURE
<222> LOCATION: (17)..(17)
<223> OTHER INFORMATION: X is any acidic amino acid or any of its amide
      form
<220> FEATURE:
<221> NAME/KEY: MISC_FEATURE
<222> LOCATION: (18)..(18)
<223> OTHER INFORMATION: X is any basic amino acid, or any
      sulfur-containing amino acid
<220> FEATURE:
<221> NAME/KEY: MISC_FEATURE
<222> LOCATION: (19)..(19)
<223> OTHER INFORMATION: X is any hydrophobic or apolar amino acid, or
      any non-aromatic hydroxyl amino acid
<220> FEATURE:
<221> NAME/KEY: MISC_FEATURE
<222> LOCATION: (20)..(20)
<223> OTHER INFORMATION: X is any basic amino acid

<400> SEQUENCE: 3

Xaa Gly Cys Cys Xaa Gly Pro Xaa Gly Cys Xaa Xaa Xaa Xaa Cys Xaa
1               5                   10                  15

Xaa Xaa Xaa Xaa Cys Cys
                20
```

COSMETIC COMPOSITION COMPRISING A MUCONOPEPTIDE

INTRODUCTION

Facial and other skin lines and wrinkles develop through a combination of aging, heredity, muscle action, sun damage and gravity. Facial and other skin expressions are made by strong muscle contractions, and over time, create skin wrinkles such as forehead lines, crow's feet and the vertical creases between the eyes. Wrinkles mostly result from a strong muscular contraction or from a prolonged time in this position. At the cellular level, the fibroblast cells synthesizing the extracellular matrix and collagen that are located along the tension lines could under the effect of muscular contractions develop particular contractile properties related to striated muscle.

The junction between a nerve and striated muscle constitutes the neuromuscular plates, upstream of which is the afferent nerve pathway, known as the motor neuron.

Muscle contraction is caused by acetylcholine, a neurotransmitter. Acetylcholine is released by the nerve that stimulates the muscle. It is known that the skin muscles of the face are under control of motor nerve afferences, and the hypoderm contains fine, flat sheets of striated muscle called the panniculus carnosus that constitute muscle tissue.

Today such mimic and age-related wrinkles are often treated with Botox (Botulinum toxin A, produced by the pathogenic microorganism *Clostridium botulinum*). Botox acts by preventing the release of acetylcholine. This toxin temporally paralyzes the muscle and inhibits contraction. Absences of contractions prevents wrinkles and induces a smooth and rejuvenated skin. Such toxins act as proteases, more specifically zinc endopeptidases targeting the neuronal cytosol: Botox B, D and F, as well as tetanus toxin produced by the *Clostridium tetani* pathogenic microorganism attack specifically VAMP (also called synaptobrevin)—a protein of synaptic vesicles; Botox A and E cleave SNAP-25 and Botox C acts on syntaxin—both proteins of the presynaptic membrane (See for example Proc. West. Pharmacol. Soc. 43:71-74, 2000).

Botox is injected locally in tissues which are thereby paralyzed. The muscles at the eyes or at the forehead don't operate any more, making the apparition of a forehead wrinkle difficult if not impossible. However, the fact that the treatment with subcutaneously injected Botox has to be conducted by a physician, its consequently high costs and its extremely high toxicity constitute considerable disadvantages. Its effectiveness lasts from 3 to 6 months, whereupon the treatment has to be repeated.

BACKGROUND

It is known from the European patent applications EP 2123673 and EP 1180524 under the name of Lipotec that peptides comprising an amino acid sequence derived from the amino acid sequence of the protein SNAP25 can compete with SNAP 25 by mimicking its N-terminal end and thus interfering in the SNARE complexes. If the SNARE complexes are destabilized, the synaptic vesicles cannot release acetylcholine efficiently and muscle contraction can be altered.

The mechanism of action of these peptides is similar to that of botulinum toxins focusing on inhibition of neuronal exocytosis of acetylcholine.

El Far Oussama and col. In Patent application WO 2011/448441 in the name of INSERM describes direct molecule interaction between VATPase and SNARE synaptobrevin (VAMP2). Soluble peptides with sequence corresponding to a portion of a VATPase subunit have the property to interfere with the neurotransmitter release.

Patent application WO 2009/012376 IN THE NAME OF University of OHIO STATE RES FOUND refers to opioid receptors that have been identified in peripheral processes of sensory neurons. Peptides have been used as delta opioid receptor agonists. This binding with the receptors inhibits the release of GABA from the nerve terminal, reducing the inhibitory effect of GABA on dopaminergic neurons.

Other peptides that are able to acts in a manner similar to Waglerin 1, a snake venom protein, acting at the post-synaptic membrane, as antagonist of the muscular nicotinic acetylcholine receptor are described in patent application WO 2006/047900 in the name of Pentapharm.

Moreover, cell membranes comprise numerous ion channels. Molecules acting as calcium channels inhibitors are for example described in the US patent application 2008/0050318 in the name of L'OREAL.

These calcium channels can be found in human fibroblasts, see for example J. Biol. Chem 267; 10524-10530, 1992 and Science 230 1024-1026, 1988.

Original peptides isolated from the venom of marine snails belonging to the family of mu-conotoxin or mu-conopeptides and acting as sodium channel inhibitors have been described in patent applications WO 2004/099238, WO 2002/07678, US 2003/050234 or WO 2007/054785. Voltage sensitive channels are key components for generating action potentials in electrically excitable cells by forming the action potential upstroke. A great diversity of sodium ion channel types and sub-types exist. All of them are voltage-sensitive sodium channel (VSSC) which open and then close in response to membrane depolarization.

The mu-conopeptides from venoms of the marine snails are able to block VSSC by blocking directly action potentials in sciatic and olfactory nerves of mouse and pike, for example. The resulting pharmacological effect consists in a block of conductance, leading to loss of function of neuromuscular system as described in the patent application WO 2007/054785 in the name of ATHERIS.

Based on their susceptibility to be blocked by tetrodotoxin (TTX), VGSCs can be divided into tetrodotoxin sensitive (TTX-S) and TTX-resistant (TTX-R) classes. These include the neuronal TTX-S type I/Nav1. 1, IiINav1.2 III/Nav1.3, PN1/Nav1.7 and PN4/Nav1.6, and the skeletal muscle TTX-S u1/Nav1.4.

Mu-conopeptides target a variety of voltage sensitive sodium channel, blocking primarily the Nav1.4 channel.

To date, no inhibitory activity on sodium channel for cosmetic application has been described or suggested for these peptides.

INVENTION

We demonstrate that mu-conopeptides make it possible to neutralize the formation of the expression skin wrinkles on human faces. They can neutralize the effects of microtensions on the skin by relaxing dermal contractile fibroblasts which are assumed to be involved in the genesis of expression wrinkles.

More particularly mu-conopeptide CnIIIC, a 23-residue peptide with three disulfide bridges, blocker of voltage-gated sodium channels particularly the muscular subtype NaV1.4, formulated as a topical product was found to induce specific actions. For example, CnIIIC reduces facial lines and wrinkles developed through aging, heredity, sun damage and gravity. These facial lines or wrinkles are characterized by furrows at the periphery of the orifices, namely the nose (nasogenic furrows), the mouth (perioral lines and bitterlines), the forehead and the eyes (crow's feet) around which the facial muscles are located.

The invention consists in a cosmetic composition comprising as an active substance a cosmetically effective amount of at least one mu-conotoxin peptide comprising the amino acid sequence:

[SEQ ID No 1]
Xaa1-Xaa2-Cys-Cys-Xaa3-Xaa4-Xaa5-Xaa6-Xaa7-Cys-

Xaa8-Xaa9-Xaa10-Xaa11-Cys-Xaa12-Xaa13-Xaa14-Xaa15-

Xaa16-Cys-Cys-Xaa17 a biologically active fragment thereof, a salt thereof, a combination thereof and/or variants thereof, and wherein Xaa1 is any N-modified amino acid,
Xaa2 is glycine,
Xaa3 is any acidic amino acid or any of its amide form,
Xaa4 is glycine,
Xaa5 is proline or 3-hydroxyl-proline,
Xaa6 is any basic amino acid,
Xaa7 is glycine,
Xaa8 is any non-aromatic hydroxyl amino acid,
Xaa9 is any non-aromatic hydroxyl amino acid,
Xaa10 is any basic amino acid,
Xaa11 is any aromatic amino acid,
Xaa2 is any basic amino acid,
Xaa13 is any acidic amino acid or any of its amide form,
Xaa14 is any basic amino acid, or any sulfur-containing amino acid,
Xaa15 is any hydrophobic or apolar amino acid, or any non-aromatic hydroxyl amino acid,
Xaa16 is any basic amino acid,
Xaa17 is absent or is any apolar amino acid, or an amide group,
optionally in combination with cosmetic acceptable carriers, diluents and/or adjuvants.

In one embodiment in the composition of the invention the mu-conotoxin peptide does not comprise at least one amino acid consisting of amino acids Xaa3, Xaa4, Xaa5, Xaa6 and Xaa7, or any combination thereof.

In one embodiment in the composition of the invention the mu-conotoxin peptide does not comprise at least one amino acid consisting of amino acids Xaa8, Xaa9, Xaa10 and Xaa111, or any combination thereof.

In one embodiment in the composition of the invention the mu-conotoxin peptide does not comprise at least one amino acid consisting of amino acids Xaa12, Xaa13, Xaa14, Xaa15 and Xaa16, or any combination thereof.

In one embodiment in the composition of the invention the N-modification of amino-acid Xaa1 in the mu-conotoxin peptide is selected from the group comprising acetylation, formylation, myristoylation or amidation:
Xaa3 and Xaa13 are independently selected from the group comprising aspartic acid (Asp), asparagine (Asn), glutamic acid (Glu), glutamine (Gln) and pyroglutamic acid (pGlu or Z);
Xaa6, Xaa10, Xaa12 and Xaa16 are independently selected from the group comprising arginine (Arg), lysine (Lys) and histidine (His);
Xaa8 and Xaa9 are independently selected from the group comprising serine (Ser) and threonine (Thr);
Xaa11 is selected from the group comprising phenylalanine (Phe), tyrosine (Tyr), and tryptophane (Trp);
Xaa14 is selected from the group comprising arginine (Arg), lysine (Lys) and histidine (His), cysteine (Cys) and methionine (Met);
Xaa15 is selected from the group comprising glycine (Gly), alanine (Ala), valine (Val), leucine (Leu) and isoleucine (Ile), serine (Ser), threonine (Thr), methionine (Met), cysteine (Cys) and proline (Pro);
Xaa17 is selected from the group comprising glycine (Gly), alanine (Ala), valine (Val), leucine (Leu), isoleucine (Ile), threonine (Thr), methionine (Met), phenylalanine (Phe) and proline (Pro).

In one embodiment in the composition of the invention in the mu-conotoxin peptide, Xaa1 is pyroglutamate (pGlu).

In one embodiment in the composition of the invention, in the mu-conotoxin peptide, the amino acid sequence is pGlu-Gly-Cys-Cys-Asn-Gly-Pro-Lys-Gly-Cys-Ser-Ser-Lys-Trp-Cys-Arg-Asp-His-Ala-Arg-Cys-Cys-amide [SEQ ID No 2], a biologically active fragment thereof, a salt thereof, a combination thereof and/or variants thereof.

The term "variant" refers to a peptide having an amino acid sequence that differ to some extent from a native sequence peptide, that is an amino acid sequence that vary from the native sequence by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence.

In one embodiment in the composition of the invention the mu-conotoxin peptide is Argninine, lysine polypeptide, CAS Number: 937286-43-6, Molecular formula $C_{92}H_{139}$, $N_{35}O_{28}S_6$ acetate salt (molar mass 2376 g/mol.).

In one embodiment the at least one mu-conotoxin peptide is present in an amount ranging from $0.05 \cdot 10^{-6}$ to $1 \cdot 10^{-4}$% by weight of the total weight of the composition.

In a further embodiment it is present in an amount ranging from $0.05 \cdot 10^{-4}$ to $0.1 \cdot 10^{-4}$% by weight of the total weight of the composition.

In a further embodiment it is present in an amount ranging from $0.1 \cdot 10^{-4}$ to $1 \cdot 10^{-4}$% by weight of the total weight of the composition.

In a further embodiment it is present in an amount ranging from $0.05 \cdot 10^{-2}$ to 1 mg/kg of the total weight of the composition.

In a further embodiment it is present in an amount ranging from 0.01 to 0.1 mg/kg of the total weight of the composition.

In a further embodiment it is present in an amount ranging from 0.1 to 1 mg/kg of the total weight of the composition.

In an embodiment the at least one mu-conotoxin peptide is present in a molar concentration ranging from 0.05 μM to 0.50 μM.

In a further embodiment it is present in a molar concentration ranging from 0.10 μM to 0.30 μM.

In a further embodiment it is present in a molar concentration ranging from 0.25 μM to 0.35 μM.

In one embodiment, the composition of the invention further comprises a cationic surfactant.

Surprisingly, the cationic surfactant enhances the cutaneous permeation of the mu-conotoxin peptide.

The cationic surfactant is chosen amongst the cationic surfactant that could be used in cosmetic compositions, like pH-dependent primary, secondary, or tertiary amines or permanently charged quaternary ammonium cations like alkyltrimethylammonium salts, Benzalkonium chloride, Dioctadecyldimethylammonium bromide or cetearyl alcohol and behentrimonium Methosulfate.

In one embodiment the cationic surfactant is present in an amount ranging from 1 to 6% by weight of the total weight of the composition.

In a further embodiment it is present in an amount ranging from 3 to 5% by weight of the total weight of the composition.

The anti-wrinkle effect could be observed from 5 minutes after the application of the composition onto the skin.

In one embodiment it could be observed from 10 minutes from the application.

In one embodiment it could be observed from 20 minutes from the application.

In one embodiment it could be observed from 20 minutes to 48 hours from the application.

The anti-wrinkle effect is observed with concentional methods know from the man skilled in the art like analysis of the skin surface carried out by calculating the standard roughness parameters.

The invention also consists in the use of a composition of the invention, to prevent and/or treat the intrinsic and extrinsic signs of skin aging: wrinkles, fine lines, discontinuities and roughness of the skin, skin sagging, skin spots and/or loss of brightness of complexion.

In one embodiment the use of a composition of the invention is to improve the mechanical properties of the skin, in terms of tonicity and/or firmness and/or elasticity of the skin.

In one embodiment the use of a composition of the invention is to improve the density of the dermis and epidermis, to give or restore volume to the dermis and epidermis.

In one embodiment the invention is a cosmetic process for treating the wrinkles comprising topically application to the skin of a composition of the invention.

More particularly it consists of applying such a composition to the areas of the face marked with wrinkles.

In one embodiment the composition of the invention is suitable for topical application to the skin and thus contains a physiologically acceptable medium, i.e., a medium that is compatible with the skin.

In one embodiment the composition may be in any presentation form normally used in cosmetics, and it may, for example, be in the form of an optionally gelled aqueous solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or O/W/O emulsion) or a vesicular dispersion of ionic and/or nonionic type. These compositions are typically prepared according to the usual methods.

In one embodiment the composition is in the form of a cream, an ointment, a milk, a lotion, a serum, a paste or a foam.

In one embodiment the composition of the invention comprises one or more additional active ingredient selected from brightening, anti-redness agents, sunscreens and UV organic or inorganic filters, hydration, moisturizing, humectants, exfoliants, anti-wrinkle, anti-ageing, slimming, anti-acne, anti-inflammatory, anti-oxidant, radical scavenger, self tanning, depilation or shave, hair growth moderator, tightening agents, peptides and vitamins.

In one embodiment the composition of the invention may comprise at least one adjuvant chosen from adjuvants such as hydrophilic and lipophilic gelling agents, hydrophilic and lipophilic active agents, preserving agents, antioxidants, solvents, fragrances, fillers, screening agents, pigments, odor absorbers and dyestuffs.

The adjuvant is present in an amount ranging, for example, from 0.01% to 50% by weight relative to the total weight of the composition.

In one embodiment the composition of the invention may also comprise at least one agent chosen from UVA-active and UVB-active organic and mineral photoprotective agents.

In one embodiment the composition of the invention is used with a device to enhance the permeation.

In a further embodiment the device is a ionophoresis device.

EXAMPLES

The product referenced as CnIIIC in the following examples is:

[SEQ ID No 2]
pGlu-Gly-Cys-Cys-Asn-Gly-Pro-Lys-Gly-Cys-Ser-Ser-
Lys-Trp-Cys-Arg-Asp-His-Ala-Arg-Cys-Cys-amide It is also referred as Arginine, lysine polypeptide, CAS Number: 937286-43-6, Molecular formula $C_{92},H_{139},N_{35},O_{28},S_6$ acetate salt (molar mass 2376 g/mol.). It is used as a mother solution which concentration is 10 µM. The mother solution is added in the final compositions in an amount ranging from 1 to 3%.

Example 1

Anti-Age Soothing Day Cream Ingredients % by Weight

Isopropyl palmitate: 20%
Cetearyl alcohol: 10%
Cetyl alcohol: 5%
Ceteareth-33: 10%
Dimethicone: 5%
Parfume: 0.5%
Preservatives: 0.5%
CnIIIC: $0.6 \cdot 10^{-4}$% (3% of the mother solution)
Water: QSP100

Example 2

Cream for Mature Skin

Carbomer: 0.2%
Glycerin: 3.5%
Potassium sorbate: 0.1%
Steareth 10: 1.5%
Cetearyl alcohol dicetyl phosphate: 3.5%
Dimethicone: 2.0%
Sorbitan stearate: 0.4%
Sodium hydroxide: 0.2%
CnIIIC: $0.2 \cdot 10^{-4}$% (1% of the mother solution)
Water: QSP 100

Example 3

Ammonium Acryloyldimethyltaurate/VP Copolymer: 0.5%
Glycerin: 3.0%
Dipropylene Glycol: 4.0%

Stearyl Alcohol: 4.0%
Jojoba Esters: 3.0%
Behentrimonium Methosulfate (and) Cetyl Alcohol (and) Butylene Glycol: 4.0%
Dimethicone: 5.0%
Dimethyl Isosorbide: 5.0%
Phenethyl Alcohol (and) Ethylhexylglycerin: 2.0%
CnIIIC: $0.6 \cdot 10^{-4}$% (3% of the mother solution)
Water: QSP 100

Example 4

Quantification of the Anti-Wrinkles Effect on Humans

The principle is to quantify the micro cutaneous relief by analyzing the deformation of networks of high-contrast lines projected on the surface under investigation on healthy human volunteers.

Parameters are quantified on a series of profiles perpendicular to the lines and wrinkles in the measurement zone.

The product was conceived for once daily application. We aimed at assessing the effect of the topical product versus placebo through an in vivo evaluation protocol, performed using a skin bioengineering method, namely in vivo fringe projection.

The concentration of the tested composition is 0.6 mg/kg so $0.6 \cdot 10^{-4}$% (w/w).

The measurements are carried out on both half of the face for the peribuccale, the crow's foot, and forehead wrinkles. They are taken using an optical system dedicated to the metrology of the relief of surfaces. The analysis of the cutaneous topography of the surface is carried out by calculating the parameters of standard roughness.

The protocol was conducted as a double-blind, active versus placebo trial, on 30 subjects over an eight hours period, during which volunteers were checked three times (T0, T2h and T8h), both clinically and for the changes of the cutaneous relief. The measurements were made using an optical system dedicated to the relief of metrology surfaces. This system includes a sensor associated with a projector and a CCD camera highresolution—Dermatop system (Eo-Tech, France)—associated with the acquisition software Optocat (EoTech, France).

The average axial and lateral resolutions are of the order of 10 microns.

At the end of the trial, tolerability was good. The enrolled volunteers expressed their full satisfaction regarding the product under study. A single acquisition is made by area. The visualization on the screen of the initial acquisition (T0) allows the correct repositioning of the Tn area.

Analysis

Analysis of the skin surface is carried out by calculating the standard roughness parameters. These parameters are extracted from an area of 30×40 mm (12 cm$^2$). Analysis of data obtained by fringe projection, on the study areas is performed through the analysis system and Toposurf Optocat.

Profile Parameter

SPt: Maximum amplitude of relief (mm).

For crow's feet, decreasing SPt means a reduction of main wrinkle. This parameter is sensitive to artifacts.

SPa: Average roughness (mm). It means changes in amplitude of the relief of the surface studied. A decrease in this parameter means a surface smoothing and a reduction of wrinkles and fine lines.

SPQ or SQ: Average of the dispersion of changes in relief (mm) using square deviation. Same interpretation as Spa even if this parameter is less sensitive to artifacts.

Morphology Parameters

Wrinkles and fine lines are detected after the use of multiple filters and correction polynomial to remove the shape and flatten the study area.

Mean area of the wrinkles (mm$^2$) This parameter corresponds to the mean area of objects (lines and wrinkles) detected in the study area.

Average volume of wrinkles (mm3). This parameter corresponds to the average volume of objects (lines and wrinkles) detected in the study area.

Average depth of wrinkles (mm). This parameter corresponds to the average depth of objects (lines and wrinkles) detected in the study area.

The results are shown in FIGS. 1, 2 and 3:

*$p<0.05$ student. Statistically significant vs T0 in favor CnIIIC.

°$p<0.05$ Wilcoxont. CnIIIC statistically different from placebo.

Figure 1:
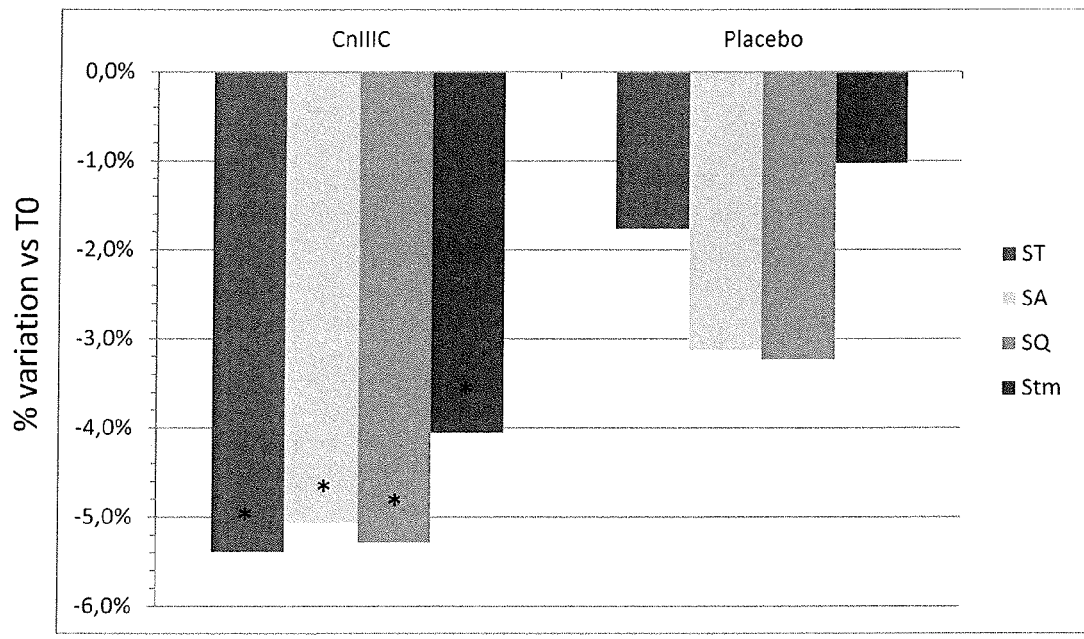
FIG. 1 shows effect of CnIIIC on Crow's feet wrinkles and rugosity.
Figure 2:
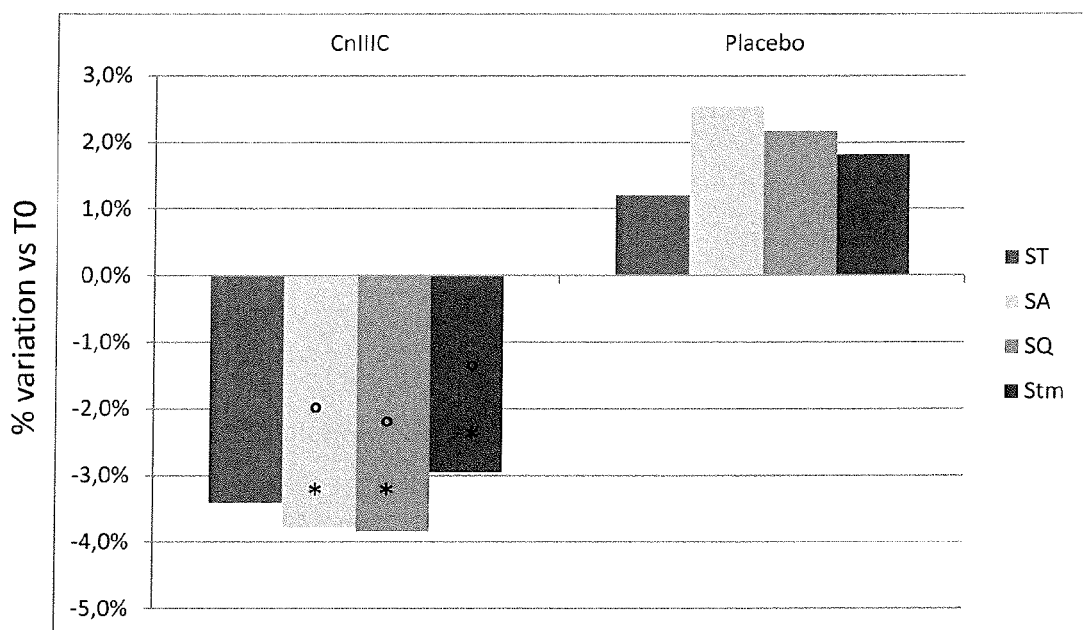
FIG. 2 shows effect of CnIIIC on forehead wrinkles and rugosity.
Figure 3:
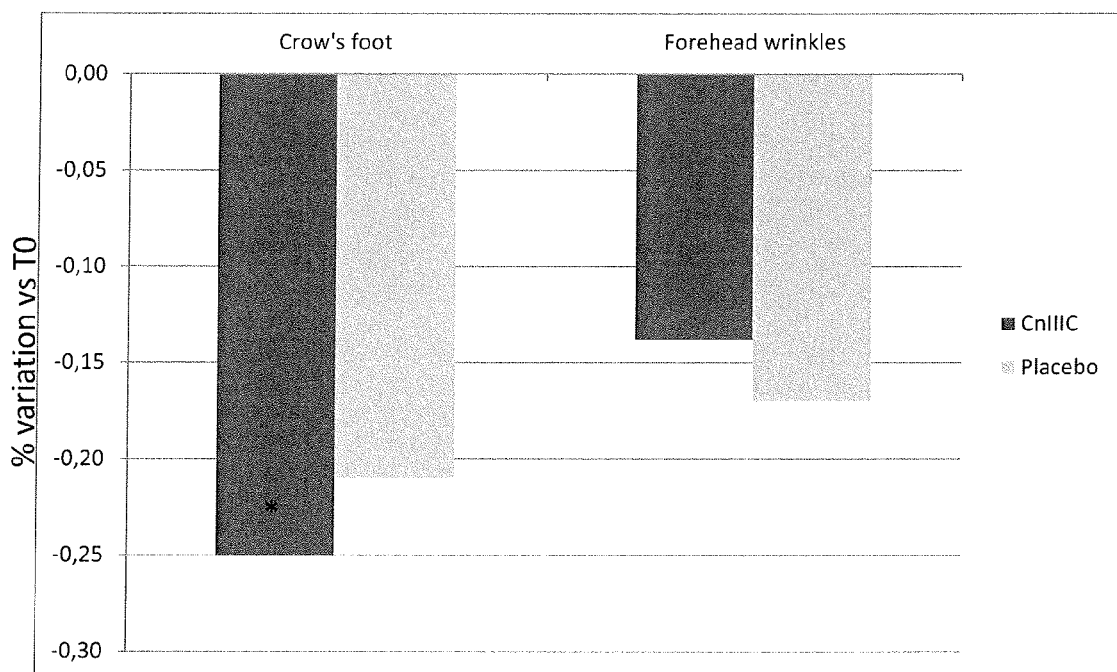
FIG. 3 represent a comparison of the effects of CnIIIC on Crow's feet and forehead wrinkles.

The results as shown in FIGS. 1, 2 and 3 demonstrate that the anti-wrinkles effect is significant. CnIIIC significantly reduces wrinkles & fine lines appearance of Crow's feet according to clinical evaluation: 5% after 2 hours of application on forehead and crows feet and more than 8% against placebo for SA parameters.

The invention claimed is:

1. A cosmetic process for treating wrinkles and fine lines comprising topically applying to the skin a composition comprising as an active substance the mu-conotoxin peptide of SEQ ID NO: 2 in an amount ranging from $0.05 \times 10^{-6}$ to $1 \times 10^{-4}$ percent by weight of the total weight of the composition.

2. The process according to claim 1, wherein the appearance of wrinkles and fine lines is reduced for 20 minutes to 48 hours after the topical application of the composition to the skin.

3. The process according to claim 2, wherein a 5% reduction in the appearance of wrinkles and fine lines is visible 2 hours after topical application of the composition to the skin.

* * * * *